(12) United States Patent
Strassner et al.

(10) Patent No.: US 11,832,823 B2
(45) Date of Patent: Dec. 5, 2023

(54) DETERMINATION OF ANVIL RELEASE DURING ANASTOMOSIS

(71) Applicant: Covidien LP, Mansfield, MA (US)

(72) Inventors: Haley E. Strassner, Hamden, CT (US); Alexander J. Hart, Tolland, CT (US); Charles R. Kollar, Washington, DC (US)

(73) Assignee: Covidien LP, Mansfield, MA (US)

( * ) Notice: Subject to any disclaimer, the term of this patent is extended or adjusted under 35 U.S.C. 154(b) by 33 days.

(21) Appl. No.: 17/666,652

(22) Filed: Feb. 8, 2022

(65) Prior Publication Data

US 2023/0248365 A1     Aug. 10, 2023

(51) Int. Cl.
*A61B 17/064*  (2006.01)
*A61B 17/115*  (2006.01)
*A61B 90/00*   (2016.01)
*A61B 17/00*   (2006.01)

(52) U.S. Cl.
CPC . *A61B 17/1155* (2013.01); *A61B 2017/00398* (2013.01); *A61B 2090/065* (2016.02)

(58) Field of Classification Search
CPC .................................................. A61B 17/1155
See application file for complete search history.

(56) References Cited

U.S. PATENT DOCUMENTS

| | | |
|---|---|---|
| 37,165 A | 12/1862 | Gary |
| 3,209,754 A | 10/1965 | Brown |
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |

(Continued)

FOREIGN PATENT DOCUMENTS

| | | |
|---|---|---|
| CN | 101683284 A | 3/2010 |
| CN | 102648864 A | 8/2012 |

(Continued)

OTHER PUBLICATIONS

Detemple, P., "Microtechnology in Modern Health Care", Med Device Technol. 9(9):18-25 (1998).

(Continued)

*Primary Examiner* — Eyamindae C Jallow
(74) *Attorney, Agent, or Firm* — Carter, DeLuca & Farrell LLP

(57) ABSTRACT

A surgical device includes a reload assembly having a plurality of staples and an anvil assembly movable relative to the reload assembly. The device also includes a power source and a motor coupled to the power source. The device further includes a transmission assembly movable by the motor and configured to move the anvil assembly relative to the reload assembly. The device additionally includes a strain sensor configured to measure strain imparted on the transmission assembly. The device also includes a controller configured to determine whether the anvil assembly is adhered to tissue grasped between the reload assembly and the anvil assembly based on the measured strain.

14 Claims, 10 Drawing Sheets

(56) References Cited

U.S. PATENT DOCUMENTS

| | | |
|---|---|---|
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |

(56) References Cited

U.S. PATENT DOCUMENTS

| | | |
|---|---|---|
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Ai-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Ai-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |

(56) References Cited

U.S. PATENT DOCUMENTS

| | | |
|---|---|---|
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,685,004 B2 | 4/2014 | Zemlock et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 10,492,814 B2 | 12/2019 | Snow et al. |
| 10,722,222 B2 | 7/2020 | Aranyi |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0006429 A1 | 1/2005 | Wales et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |

(56) References Cited

U.S. PATENT DOCUMENTS

| | | | |
|---|---|---|---|
| 2012/0193393 | A1 | 8/2012 | Viola et al. |
| 2012/0198288 | A1 | 8/2012 | Njo et al. |
| 2012/0220989 | A1 | 8/2012 | Zemlok et al. |
| 2012/0223121 | A1 | 9/2012 | Viola et al. |
| 2012/0241494 | A1 | 9/2012 | Marczyk |
| 2012/0277790 | A1 | 11/2012 | Zemlok et al. |
| 2012/0298718 | A1 | 11/2012 | Marczyk |
| 2012/0298720 | A1 | 11/2012 | Marczyk |
| 2015/0129635 | A1 | 5/2015 | Williams et al. |
| 2020/0054337 | A1* | 2/2020 | Sgroi, Jr. ............ A61B 17/1155 |
| 2020/0405304 | A1* | 12/2020 | Mozdzierz ....... A61B 17/07207 |
| 2021/0128153 | A1* | 5/2021 | Sgroi ..................... A61B 90/98 |
| 2022/0387022 | A1* | 12/2022 | Knapp ............... A61B 17/1155 |
| 2022/0409208 | A1* | 12/2022 | Strassner ........... A61B 17/1155 |

FOREIGN PATENT DOCUMENTS

| | | | |
|---|---|---|---|
| EP | 0537570 | A2 | 4/1993 |
| EP | 0647431 | A2 | 4/1995 |
| EP | 0738501 | A1 | 10/1996 |
| EP | 0770354 | A1 | 5/1997 |
| EP | 1070487 | A2 | 1/2001 |
| EP | 1201196 | A1 | 5/2002 |
| EP | 1658817 | A1 | 5/2006 |
| EP | 1813203 | A2 | 8/2007 |
| FR | 2849589 | A1 | 7/2004 |
| WO | 9414129 | A1 | 6/1994 |
| WO | 9729694 | A1 | 8/1997 |
| WO | 9740760 | A1 | 11/1997 |
| WO | 9837825 | A1 | 9/1998 |
| WO | 9952489 | A1 | 10/1999 |
| WO | 0234140 | A2 | 5/2002 |
| WO | 03026511 | A1 | 4/2003 |
| WO | 03030743 | A2 | 4/2003 |
| WO | 2004032760 | A2 | 4/2004 |
| WO | 2007030753 | A2 | 3/2007 |
| WO | 2007114868 | A2 | 10/2007 |
| WO | 2007118179 | A2 | 10/2007 |
| WO | 2007014355 | A3 | 4/2009 |
| WO | 2009143092 | A1 | 11/2009 |

OTHER PUBLICATIONS

Abridged Data Sheet, "DeepCover Secure Authenticator with 1-Wire SHA-256 and 512-Bit User EEPROM", Maxim Integrated Products, Inc. pp 1-4; 42; Dec. 2012.

Data Sheet "DS28E15-1-Sire SHA-256 Secure Authenticator with 512-Bit User EEPROM" ; IC-ON-LINE, Electronic Component Manufacturers, pp. 1-2; Aug. 2013.

Extended European Search Report issued in corresponding application EP 23155411.4 dated Jun. 7, 2023 (10 pages).

\* cited by examiner

DETERMINATION OF ANVIL RELEASE DURING ANASTOMOSIS

BACKGROUND

1. Technical Field

The present disclosure relates to surgical devices. More specifically, the present disclosure relates to handheld electromechanical surgical systems for performing surgical procedures.

2. Background of Related Art

Circular staplers are used in a surgical procedure to reattach rectum portions that were previously transected, or similar procedures. Circular clamping, cutting and stapling instruments may be manually actuated and may include a pistol or linear grip-styled structure having an elongated shaft extending therefrom and a staple cartridge supported on the distal end of the elongated shaft. A physician may insert an anvil assembly of the circular stapling instrument through an incision and toward the transected rectum portions. The physician may also insert the remainder of the circular stapling instrument (including the cartridge assembly) into a rectum of a patient and maneuver the instrument up the colonic tract of the patient toward the transected rectum portions. The anvil and cartridge assemblies are approximated toward one another, and staples are ejected from the cartridge assembly toward the anvil assembly to form the staples in tissue to affect an end-to-end anastomosis, and an annular knife is advanced to core a portion of the clamped tissue portions. After the end-to-end anastomosis has been affected, the circular stapling apparatus is removed from the surgical site. Powered surgical staplers have also been developed and utilize one or more motors to clamp, cut, and staple tissue.

In certain cases, with manual and powered circular staplers, the anvil may not fully release from the anastomosis during anvil extraction. This may threaten the integrity of anastomosis as tension of stress on the tissue may affect the tissue health or staple line integrity. Therefore, surgeons must currently closely monitor removal forces and remove the device slowly and with care, occasionally manipulating the device to ensure the anvil is released from the anastomosis.

SUMMARY

The present disclosure provides a powered circular stapler that is configured to operate in three sequences, namely, clamping, stapling, and cutting to form an anastomosis by connecting two portions of a structure (e.g., intestine, colon, etc.). The powered circular stapler includes a handle assembly having a power source and one or more motors coupled to the power source. The stapler also includes an adapter assembly having multiple transmission assemblies, e.g., drive shafts, which transmit actuation from the powered handle. The powered handle assembly and the adapter assembly may be reusable.

The powered surgical staplers operate in four phases, namely, clamping, stapling, cutting, and unclamping. Clamping is accomplished by moving the anvil in a proximal direction to compress tissue between the anvil and a reload assembly, which includes a plurality of staples. The anvil and the reload assembly may be disposable. During stapling, the staples are ejected from the reload assembly into the clamped tissue and are deformed against the anvil. Cutting includes moving an annular knife through the compressed and stapled tissue until the knife contacts the anvil. During unclamping, the anvil assembly is moved distally away from the cut tissue and the reload assembly.

The anvil includes a breakable retainer configured to secure a cutting ring, i.e., the surface that contact the annular knife, inside a tiltable anvil head of the anvil assembly. Upon breaking of the retainer member, the cutting ring is pushed into the anvil. In addition, the breakage of the retainer also allows the anvil head to tilt, such that as the anvil is moved away from the reload, the anvil head is released from the tissue and is tilted.

Each of the clamping, stapling, cutting, and unclamping phases may be monitored to ensure proper operation of the powered surgical stapler, including proper anvil release after the cutting process is complete. The powered surgical stapler also includes a sensor, e.g., a strain gauge, configured to measure forces during each of the processes, and a controller configured to monitor the forces and detect any abnormalities during operation of the powered surgical stapler. In particular, the controller is configured to monitor forces during unclamping and identify any unexpected forces on the anvil assembly. If such forces are detected, this may be due to the anvil not being released from the anastomosis. Thus, the controller may pause and/or terminate the unclamping process to prevent any damage to the powered surgical stapler and/or injury to the anastomosis. The controller may be also configured to alert the user to intervene, e.g., manually release the anvil assembly, in the unclamping process.

According to one embodiment of the present disclosure, a surgical device is disclosed. The surgical device includes a reload assembly having a plurality of staples and an anvil assembly movable relative to the reload assembly. The device also includes a power source and a motor coupled to the power source. The device further includes a transmission assembly movable by the motor and configured to move the anvil assembly relative to the reload assembly. The device additionally includes a strain sensor configured to measure strain imparted on the transmission assembly. The device also includes a controller configured to determine whether the anvil assembly is adhered to tissue grasped between the reload assembly and the anvil assembly based on the measured strain.

Implementations of the above embodiment may include one or more of the following features. According to one aspect of the above embodiment, the anvil assembly may include: a rod; an anvil head pivotable from a tilt position to a non-tilt position relative to the rod; and a retainer is configured to maintain the anvil head in the non-tilt position. The anvil assembly may further include a cutting ring coupled to the retainer. The cutting ring may be configured to at least one of deform or break the retainer. The controller may be further configured to determine that the anvil assembly is tilted based on a change in measured strain indicative of at least one of deformation or breakage of the retainer. The controller may be also configured to determine whether the anvil assembly is movable during unclamping. The surgical device may also include a longitudinal shaft enclosing the transmission assembly. The strain sensor may be disposed in the longitudinal shaft and contacts the transmission assembly.

According to another embodiment of the present disclosure, a surgical device is disclosed. The surgical device includes a reload assembly having a plurality of staples and an anvil assembly movable relative to the reload assembly.

The device also includes a power source, a first motor coupled to the power source, and a first transmission assembly movable by the first motor and configured to move the anvil assembly relative to the reload assembly. The device further includes a second motor coupled to the power source, a second transmission assembly movable by the second motor and configured to move a knife assembly to cut tissue grasped between the reload assembly and the anvil assembly. The device additionally includes a strain sensor configured to measure strain imparted on the first transmission assembly and the second transmission assembly. The device further includes a controller configured to determine whether the anvil assembly is adhered to the tissue based on the measured strain.

Implementations of the above embodiment may include one or more of the following features. According to one aspect of the above embodiment, the anvil assembly may include: a rod; an anvil head pivotable from a tilt position to a non-tilt position relative to the rod; and a retainer is configured to maintain the anvil head in the non-tilt position. The anvil assembly may further include a cutting ring coupled to the retainer and to contact the knife. The cutting ring may be configured to at least one of deform or break the retainer. The controller may be further configured to determine the anvil assembly is tilted based on a change in measured strain indicative of at least one of deformation or breakage of the retainer. The controller may be also configured to determine whether the anvil assembly is movable during unclamping. The surgical device may also include a longitudinal shaft enclosing at least a portion of each of the first transmission assembly and the second transmission assembly. The strain sensor may be disposed in the longitudinal shaft and contact the first transmission assembly and the second transmission assembly.

According to a further embodiment of the present disclosure, a method for controlling a powered surgical stapler is disclosed. The method includes activating a first motor to move a first transmission assembly coupled to an anvil assembly that is movable relative to a reload assembly having a plurality of staples. The method also includes activating a second motor to move a second transmission assembly coupled to a knife assembly configured to cut tissue grasped between the reload assembly and the anvil assembly. The method further includes measuring through a strain sensor, strain imparted on the first transmission assembly and the second transmission assembly. The method additionally includes determining, at a controller, whether the anvil assembly is adhered to the tissue based on the measured strain.

Implementations of the above embodiment may include one or more of the following features. According to one aspect of the above embodiment, the method may also include pivoting an anvil head of the anvil assembly and securing the anvil head in a non-tilted position using a retainer. The method further includes determining, at the controller, that the anvil assembly is tiltable based on a change in measured strain indicative of at least one of deformation or breakage of the retainer. The method also includes determining, at the controller, whether the anvil assembly is movable during unclamping.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
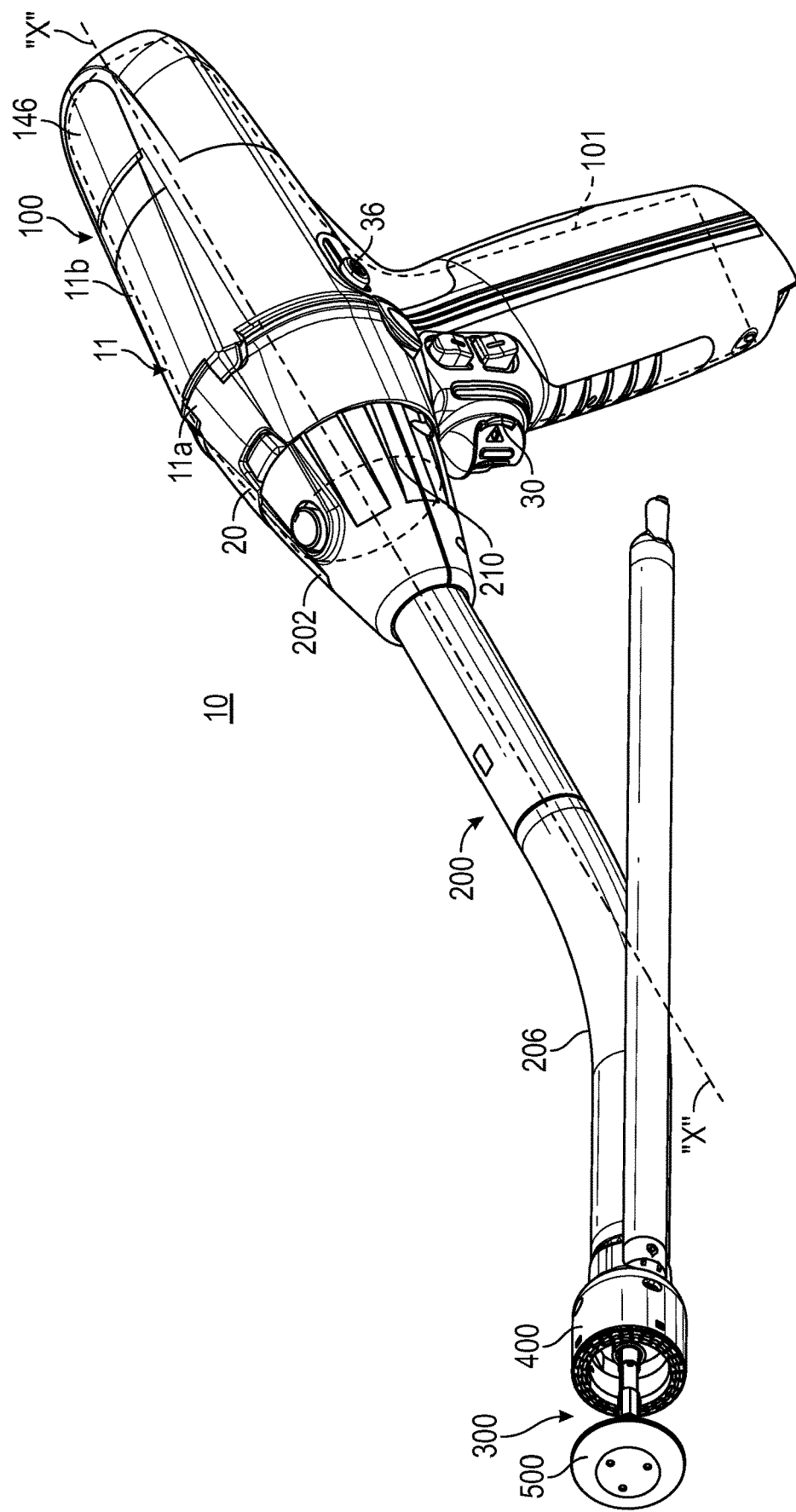
FIG. 1 is a perspective view of a powered circular stapler including a handle assembly, an adapter assembly, and an end effector, according to an embodiment of the present disclosure.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the surgical instrument, or component thereof, farther from the user, while the term "proximal" refers to that portion of the surgical instrument, or component thereof, closer to the user.

The present disclosure provides a powered circular stapler 10 having a handle assembly, an adapter assembly coupled to the handle assembly, and an end effector coupled to the adapter assembly. The stapler allows for full, independent control of three functions: clamping, stapling, and cutting. This allows certain portions of the stapler to adapt if the tissue presents a non-ideal situation.

FIG. 1 illustrates a surgical device, such as, for example, a powered circular stapler 10 for forming end-to-end anastomosis ("EEA"), including a handle assembly 100, which is configured for selective connection with an adapter assembly 200. The adapter assembly 200 is configured for selective connection with an end effector 300, which includes a reload 400 and an anvil assembly 500. The end effector 300 is configured to produce a surgical effect on tissue of a patient, namely, forming an anastomosis by connecting two portions of a structure (e.g., intestine, colon, etc.) by clamping, stapling, and cutting tissue grasped within the end effector 300.

The handle assembly 100 includes a power handle 101 and an outer shell housing 11 configured to selectively receive and encase power handle 101. The shell housing 11 includes a distal half-section 11a and a proximal half-section 11b pivotably connected to distal half-section 11a. When joined, distal and proximal half-sections 11a, 11b define a shell cavity therein in which power handle 101 is disposed.

While the powered circular stapler 10 is described herein as a modular device including a plurality of interconnected components, such as the handle assembly 100, the removable shell housing 11, and the adapter assembly 200, etc. The powered circular stapler 10 may be formed as an integrated device with one or more of the components being securely attached to each other, e.g., during manufacturing of the powered circular stapler.

Distal and proximal half-sections 11a, 11b of shell housing 11 are divided along a plane that traverses a longitudinal axis "X" of adapter assembly 200. Distal half-section 11a of shell housing 11 defines a connecting portion 20 configured to accept a corresponding drive coupling assembly 210 (FIG. 3) of adapter assembly 200. Distal half-section 11a of shell housing 11 supports a toggle control button 30. Toggle control button 30 is capable of being actuated in four directions (e.g., a left, right, up, and down).

Figure 2:
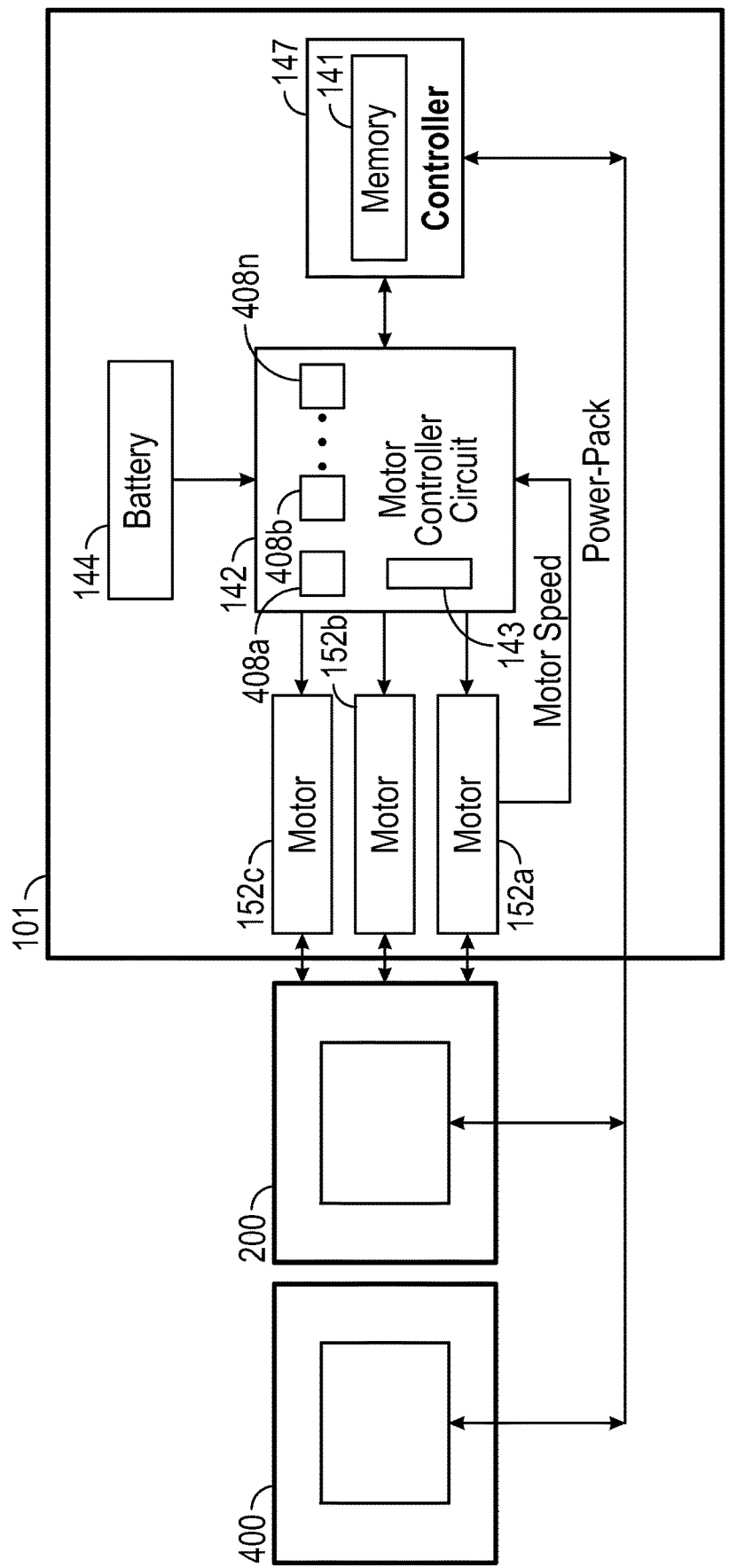
FIG. 2 is a schematic diagram of the handle assembly, the adapter assembly, and the end effector of FIG. 1.

With reference to FIGS. 1 and 2, the power handle 101 includes a main controller circuit board 142, a rechargeable battery 144 configured to supply power to any of the electrical components of handle assembly 100, and a plurality of motors, i.e., a first motor 152a, a second motor 152b, a third motor 152c coupled to the battery 144. The power handle 101 also includes a display 146. In embodiments, the motors 152a, 152b, 152c may be coupled to any suitable power source configured to provide electrical energy to the motors 152a, 152b, 152c, such as an AC/DC transformer. Each of the motors 152a, 152b, 152c is coupled a motor controller 143 which controls the operation of the corresponding motors 152a, 152b, 152c including the flow of electrical energy from the battery 144 to the motors 152a, 152b, 152c. A main controller 147 is provided that controls the power handle 101. The main controller 147 is configured to execute software instructions embodying algorithms disclosed herein, such as clamping, stapling, and cutting algorithms which control operation of the power handle 101.

The motor controller 143 includes a plurality of sensors 408a . . . 408n configured to measure operational states of the motors 152a, 152b, 152c and the battery 144. The sensors 408a-n include a strain gauge 408b and may also include voltage sensors, current sensors, temperature sensors, telemetry sensors, optical sensors, and combinations thereof. The sensors 408a-408n may measure voltage, current, and other electrical properties of the electrical energy supplied by the battery 144. The sensors 408a-408n may also measure angular velocity (e.g., rotational speed) as revolutions per minute (RPM), torque, temperature, current draw, and other operational properties of the motors 152a, 152b, 152c. The sensor 408a also includes an encoder configured to count revolutions or other indicators of the motors 152a, 152b, 152c, which is then use by the main controller 147 to calculate linear movement of components movable by the motors 152a, 152b, 152c. Angular velocity may be determined by measuring the rotation of the motors 152a, 152b, 152c or a drive shaft (not shown) coupled thereto and rotatable by the motors 152a, 152b, 152c. The position of various axially movable drive shafts may also be determined by using various linear sensors disposed in or in proximity to the shafts or extrapolated from the RPM measurements. In embodiments, torque may be calculated based on the regulated current draw of the motors 152a, 152b, 152c at a constant RPM. In further embodiments, the motor controller 143 and/or the main controller 147 may measure time and process the above-described values as a function of time, including integration and/or differentiation, e.g., to determine the rate of change in the measured values. The main controller 147 is also configured to determine distance traveled of various components of the adapter assembly 200 and/or the end effector 300 by counting revolutions of the motors 152a, 152b, 152c.

The motor controller 143 is coupled to the main controller 147, which includes a plurality of inputs and outputs for interfacing with the motor controller 143. In particular, the main controller 147 receives measured sensor signals from the motor controller 143 regarding operational status of the motors 152a, 152b, 152c and the battery 144 and, in turn, outputs control signals to the motor controller 143 to control the operation of the motors 152a, 152b, 152c based on the sensor readings and specific algorithm instructions. The main controller 147 is also configured to accept a plurality of user inputs from a user interface (e.g., switches, buttons, touch screen, etc. coupled to the main controller 147).

The main controller 147 is also coupled to a memory 141. The memory 141 may include volatile (e.g., RAM) and non-volatile storage configured to store data, including software instructions for operating the power handle 101. The main controller 147 is also coupled to the strain gauge 408b of the adapter assembly 200 using a wired or a wireless connection and is configured to receive strain measurements from the strain gauge 408b which are used during operation of the power handle 101.

The power handle 101 includes a plurality of motors 152a, 152b, 152c each including a respective motor shaft (not explicitly shown) extending therefrom and configured to drive a respective transmission assembly. Rotation of the motor shafts by the respective motors function to drive shafts and/or gear components of adapter assembly 200 in order to perform the various operations of handle assembly 100. In particular, motors 152a, 152b, 152c of power handle 101 are configured to drive shafts and/or gear components of adapter assembly 200 in order to selectively extend/retract a trocar member 274 (FIG. 4) of a trocar assembly 270 of adapter assembly 200. Extension/retraction of the trocar member 274 opens/closes end effector 300 (when anvil assembly 500 is connected to trocar member 274 of trocar assembly 270), fire an annular array of staples 423 of reload 400, and move an annular knife 444 of reload 400.

Figure 3:
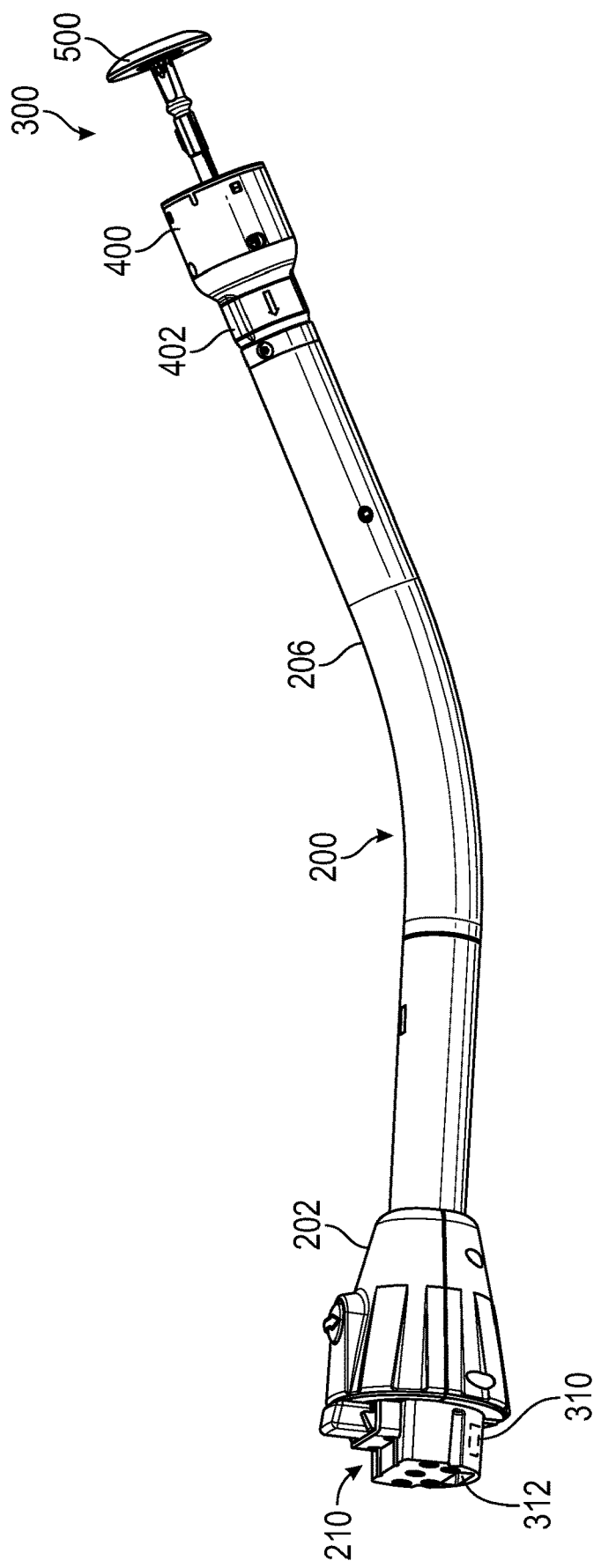
FIG. 3 is a side perspective view of the adapter assembly and the end effector, an annular reload and an anvil assembly, attached to the adapter assembly of FIG. 1 according to an embodiment of the present disclosure.
Figure 4:
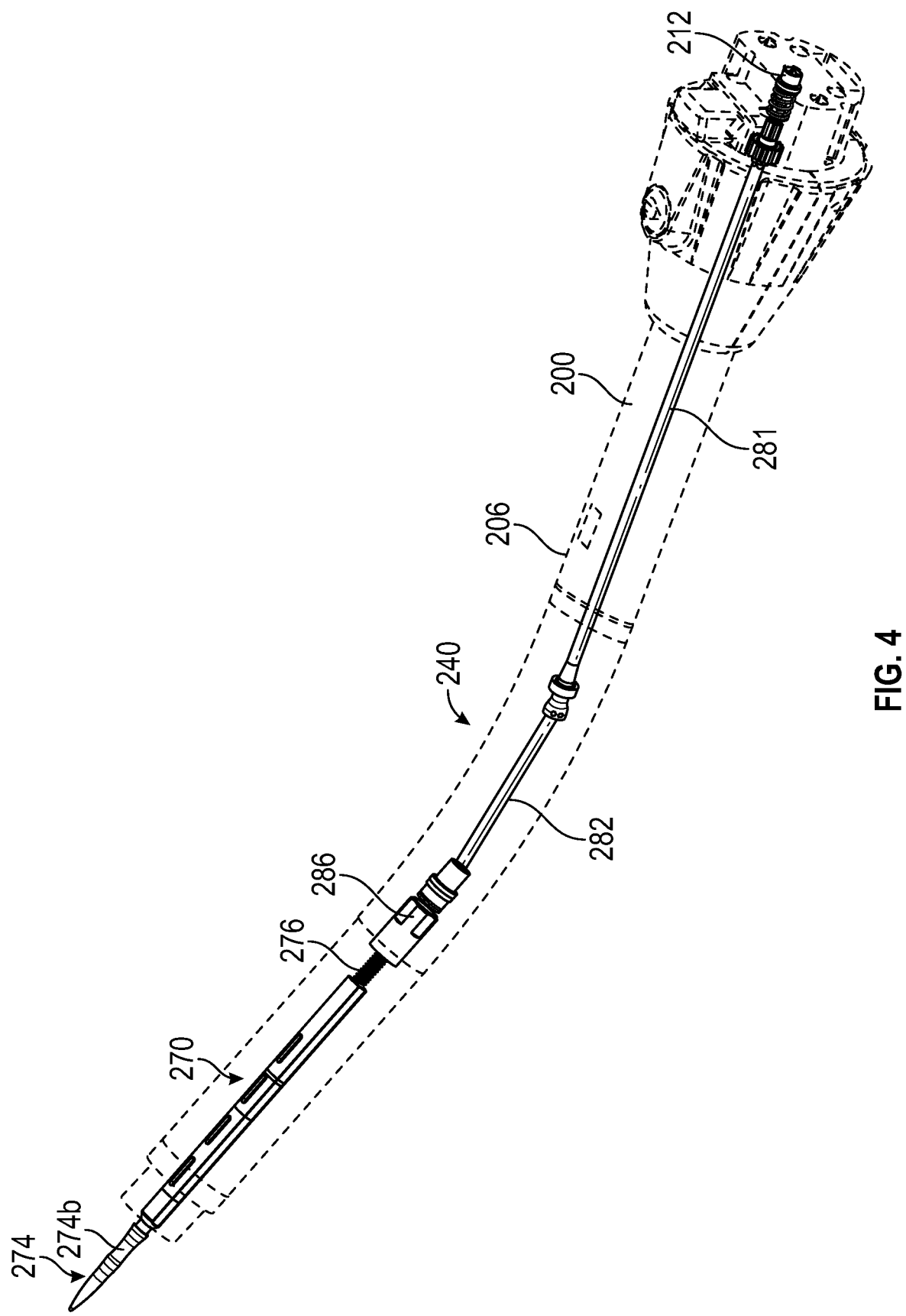
FIG. 4 is a perspective view of a clamping transmission assembly disposed within the adapter assembly of FIG. 1, shown partially in phantom.

Turning now to FIGS. 3 and 4, adapter assembly 200 includes an outer knob housing 202 and an outer tube 206 extending from a distal end of knob housing 202. Knob housing 202 and outer tube 206 are configured and dimensioned to house the components of adapter assembly 200. The knob housing 202 includes an electrical connector 312 and a storage device 310 coupled thereto. The storage device 310 is configured to store various operating parameters pertaining to the adapter assembly 200. Adapter assembly 200 is configured to convert rotation of coupling shafts (not explicitly shown) of handle assembly 100 into axial translations useful for operating trocar assembly 270 of adapter assembly 200, anvil assembly 500, and/or staple driver 430 or knife assembly 440 of reload 400.

Adapter assembly 200 further includes the trocar assembly 270 removably supported in a distal end of outer tube 206. Trocar assembly 270 includes a trocar member 274 and a drive screw 276 operably received within trocar member 274 for axially moving trocar member 274 relative to outer tube 206. A distal end 274b of trocar member 274 is configured to selectively engage anvil assembly 500, such that axial movement of trocar member 274, via a rotation of drive screw 276, results in a concomitant axial movement of anvil assembly 500.

With reference to FIG. 4, a clamping transmission assembly 240 includes first rotatable proximal drive shaft 212 coupled to the first motor 152a, a second rotatable proximal drive shaft 281, a rotatable distal drive shaft 282, and a coupling member 286, each of which are supported within the outer tube 206 of adapter assembly 200. Clamping transmission assembly 240 functions to extend/retract trocar member 274 of trocar assembly 270 of adapter assembly 200, and to open/close the anvil assembly 510 when anvil assembly 510 is connected to trocar member 274.

Figure 5:
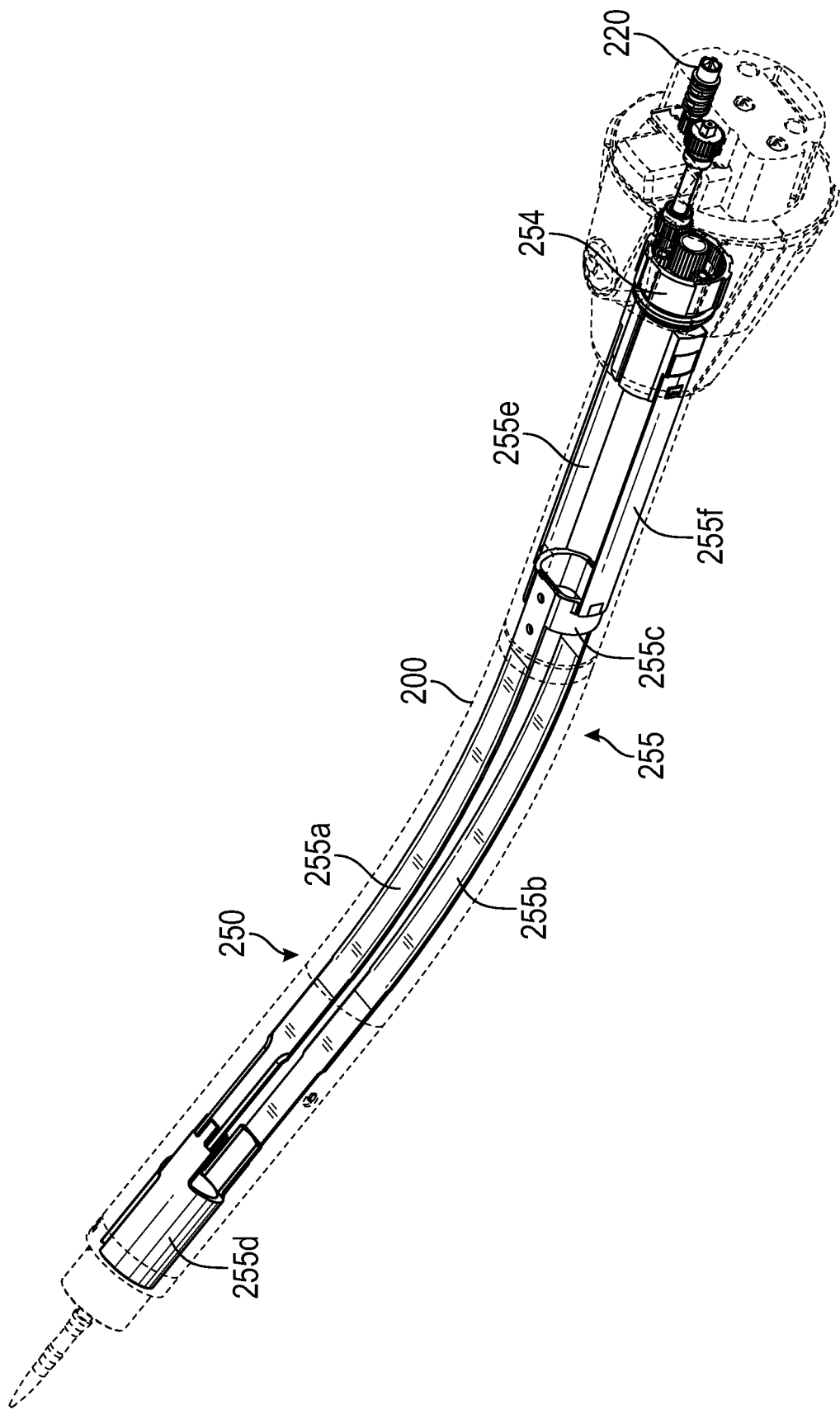
FIG. 5 is a perspective view of a stapling transmission assembly disposed within the adapter assembly of FIG. 1, shown partially in phantom.

With reference to FIG. 5, the adapter assembly 200 includes a stapling transmission assembly 250 for interconnecting the second motor 152b and a second axially translatable drive member of reload 400, wherein the stapling transmission assembly 250 converts and transmits a rotation of the second motor 152b to an axial translation of an outer flexible band assembly 255 of adapter assembly 200, and in turn, the staple driver 430 of reload 400 to fire staples 423 from the reload 400 and against anvil assembly 510.

The stapling transmission assembly 250 of adapter assembly 200 includes the outer flexible band assembly 255 secured to staple driver coupler 254. A second rotatable proximal drive shaft 220 is coupled to the second motor 152b and is configured to actuate that staple driver coupler 254, which converts rotational movement into longitudinal movement. Outer flexible band assembly 255 includes first and second flexible bands 255a, 255b laterally spaced and connected at proximal ends thereof to a support ring 255c and at distal ends thereof to a proximal end of a distal pusher 255d. Each of first and second flexible bands 255a, 255b is attached to support ring 255c and distal pusher 255d. Outer flexible band assembly 255 further includes first and second connection extensions 255e, 255f extending proximally from support ring 255c. First and second connection extensions 255e, 255f are configured to operably connect outer flexible band assembly 255 to staple driver coupler 254 of stapling transmission assembly 250.

Figure 6:
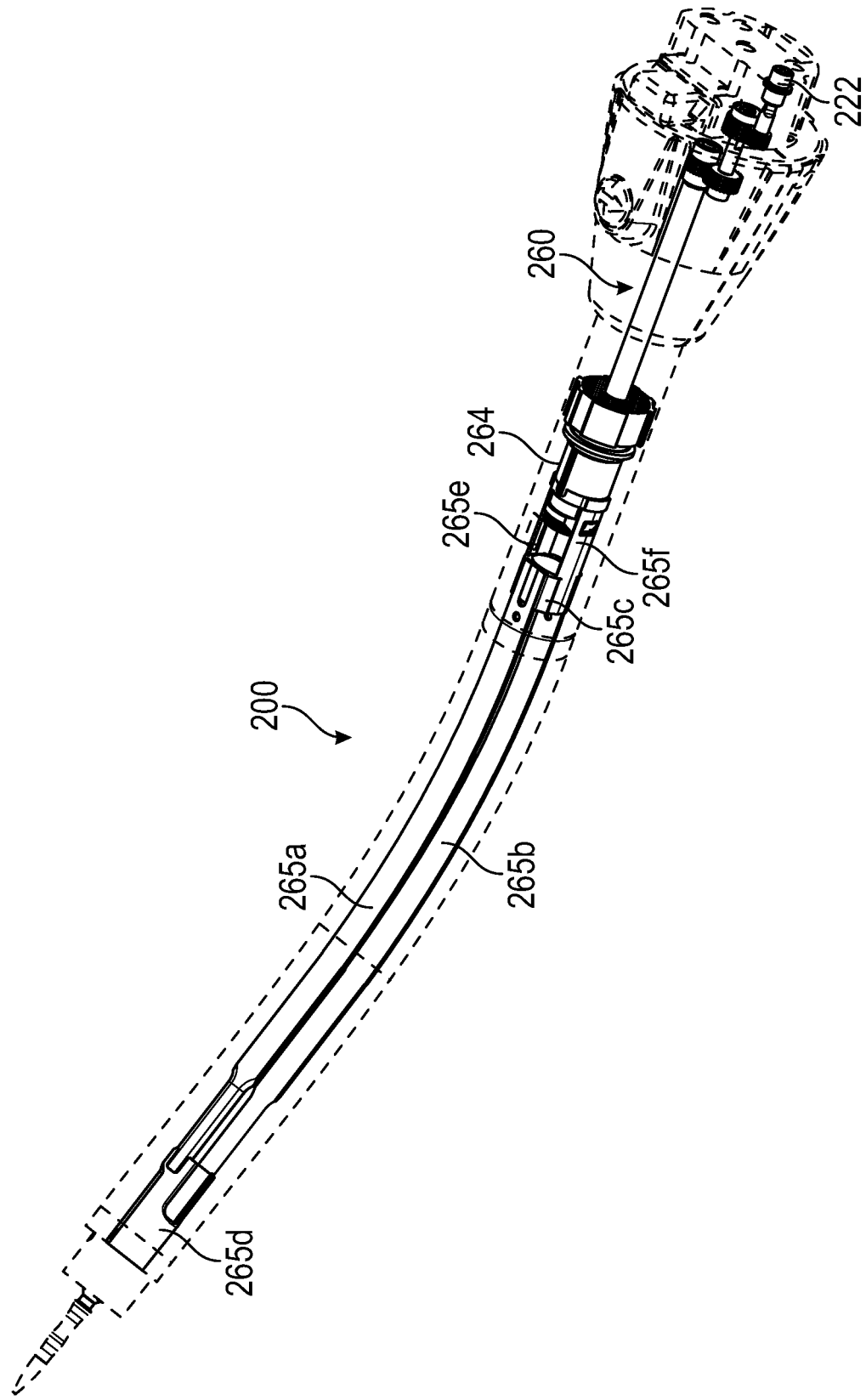
FIG. 6 is a perspective view of a cutting transmission assembly disposed within the adapter assembly of FIG. 1, shown partially in phantom.

With reference to FIG. 6, the adapter assembly 200 also includes a cutting transmission assembly 260 having a third rotatable proximal drive shaft 222 for interconnecting the third motor 152c and the annular knife 444 of reload 400, wherein the cutting transmission assembly 260 converts and transmits a rotation of one of the third motor 152c to an axial translation of an outer flexible band assembly 265 of adapter assembly 200, and in turn, a knife carrier 442 of reload 400 to advance the annular knife 444 from the reload 400 and against anvil assembly 510.

Inner flexible band assembly 265 includes first and second flexible bands 265a, 265b laterally spaced and connected at proximal ends thereof to a support ring 265c and at distal ends thereof to a proximal end of a support base 265d. Each of first and second flexible bands 265a, 265b are attached to support ring 265c and support base 265d.

Inner flexible band assembly 265 further includes first and second connection extensions 265e, 265f extending proximally from support ring 265c. First and second connection extensions 265e, 265f are configured to operably connect inner flexible band assembly 265 to knife driver 264 of cutting transmission assembly 260. Support base 265d extends distally from flexible bands 265a, 265b and is configured to connect with a knife assembly 440 of reload 400.

Figure 7:
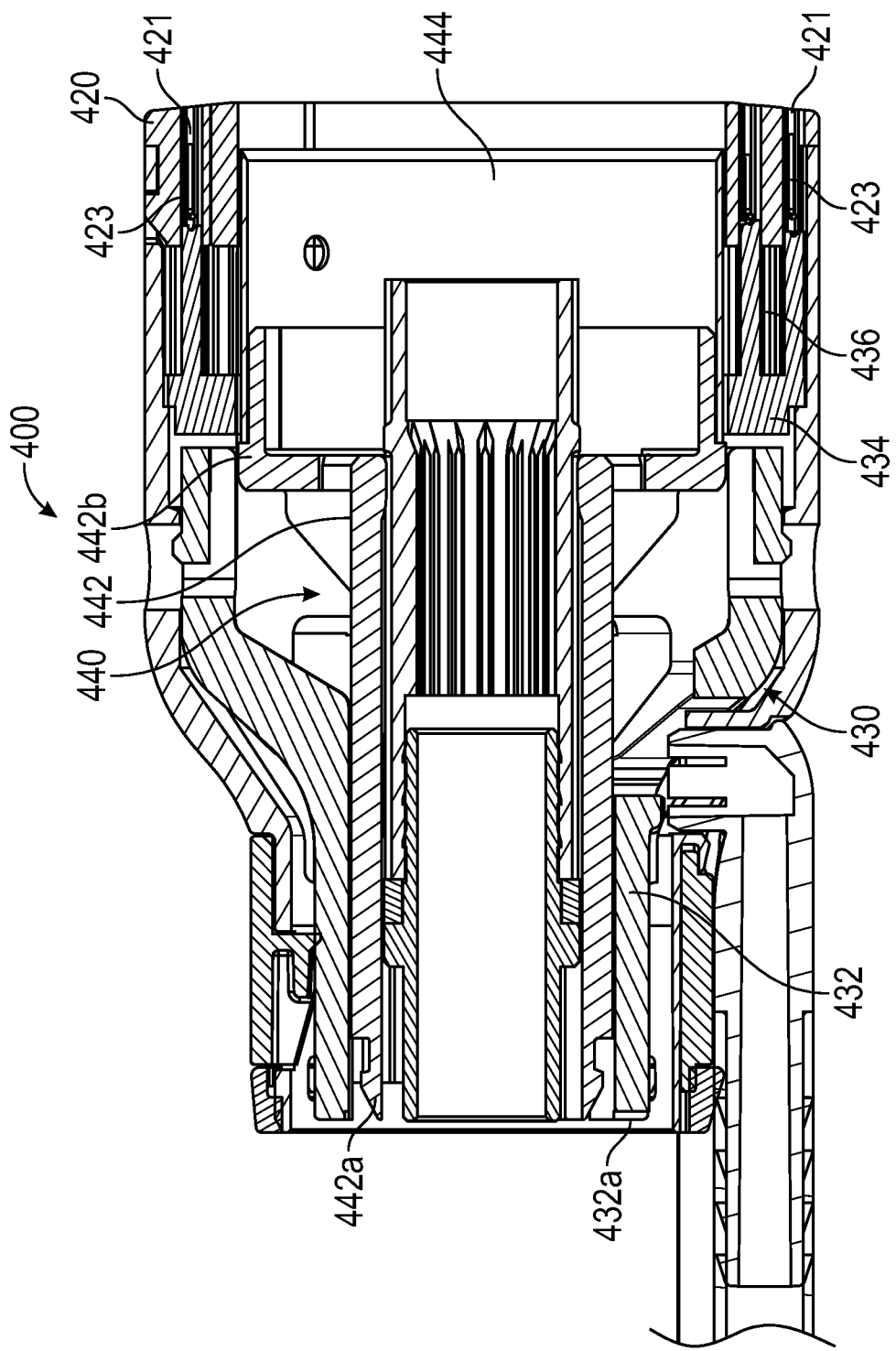
FIG. 7 is a cross-sectional view of a reload of the end effector of FIG. 1.

With reference to FIG. 7, staple driver 430 of reload 400 includes a staple cartridge 420 having a driver adapter 432 and a driver 434. A proximal end 432a of driver adapter 432 is configured for selective contact and abutment with distal pusher 255d of outer flexible band assembly 255 of stapling transmission assembly 250 of adapter assembly 200. In operation, during distal advancement of outer flexible band assembly 255, as described above, distal pusher 255d of outer flexible band assembly 255 contacts proximal end 432a of driver adapter 432 to advance driver adapter 432 and driver 434 from a first or proximal position to a second or distal position. Driver 434 includes a plurality of driver members 436 aligned with staple pockets 421 of staple cartridge 420 for contact with staples 423. Accordingly, advancement of driver 434 relative to staple cartridge 420 causes ejection of the staples 423 from staple cartridge 420.

The knife assembly 440 of the reload 400 includes a knife carrier 442 and an annular knife 444 secured about a distal end 442b of knife carrier 442. A proximal end 442a of knife carrier 442 is configured to engage the support base 265d of inner flexible band assembly. In operation, during distal advancement of inner flexible band assembly 265, support base 265d of inner flexible band assembly 265 connects with proximal end 442a of knife carrier 442 to advance knife carrier 442 and annular knife 444 from a first or proximal position to a second or advanced position to cause the cutting of tissue disposed between staple cartridge 420 and anvil assembly 510.

Forces during an actuation of trocar member 274, closing of end effector 300 (e.g., a retraction of anvil assembly 500 relative to reload 400), ejecting staples 423 from the reload 400, and advancement of the knife assembly 440 may be measured by the strain gauge 408b in order to monitor and control various processes, such as firing of staples 423 from reload 400; monitor forces during a firing and formation of the staples 423 as the staples 423 are being ejected from reload 400; optimize formation of the staples 423 (e.g., staple crimp height) as the staples 423 are being ejected from reload 400 for different indications of tissue; and monitor and control a firing of the annular knife of reload 400.

Figure 8:
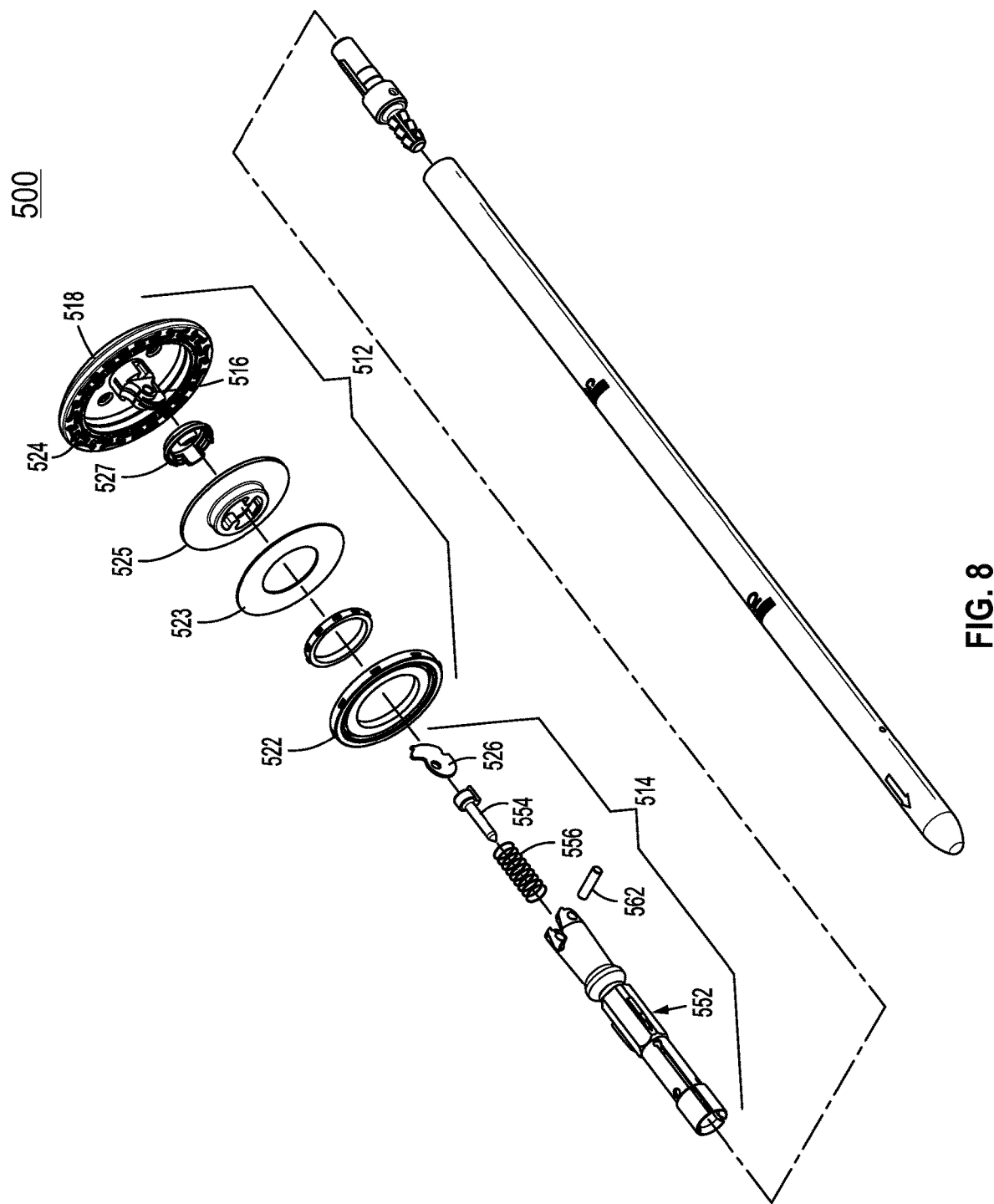
FIG. 8 is a perspective view, with parts separated, of the anvil assembly of FIG. 1.

With reference FIG. 8, the anvil assembly 500 includes a head assembly 512 and a center rod assembly 514. Head assembly 512 includes a post 516, a housing 518, a cutting ring 522, a cutting ring cover 523, an anvil plate 524, a spacer or washer 525, a cam latch member 526, and a retainer member 527. Post 516 is centrally positioned within housing 518. The anvil plate 524 is supported in an outer annular recess 528 of an anvil housing 518 and includes a plurality of staple pockets 530 formed therein and configured to receive and form staples.

The cutting ring 522 includes a central opening which is positioned about a post 516 within an inner annular recess of the housing 518 between post 516 and the outer annular recess 528. The cutting ring 522 may be formed from any suitable material, such as a metal or a polymer, e.g., polyethylene. A cutting ring cover 523 is also secured to an outwardly facing or proximal surface of the cutting ring 522.

The retainer member 527 positioned in the inner annular recess between cutting ring 522 and a back wall of housing 518. Retainer member 527 may have an annular shape and may include a plurality of deformable tabs which engage a rear surface of cutting ring 522. The retainer member 527 prevents the cutting ring 522 from moving or being pushed into the inner annular recess of housing 518 until a predetermined force sufficient to break and/or deform the tabs has been applied to cutting ring 522. During cutting of tissue the annular knife 444 is advanced until the annular knife 444 contacts the cutting ring 522. Continuous pressure by the annular knife 444 on the cutting ring 522 results in breakage of the retainer member 527, which allows the cutting ring 522 to move into the housing 518 and separate from the tissue. This allows for separation of the anvil assembly 500 from the tissue and facilitates the unclamping process.

Cam latch member 526 is pivotally mounted within a transverse slot of post 516 of housing 518 and about pivot member 562. Cam latch member 526 has an outer cam profile which permits plunger 554 to move forward as cam latch member 526 rotates in a clockwise direction and permits plunger 554 to be retracted as cam latch member 526 rotates in a counterclockwise direction.

Plunger 554 is slidably positioned in a bore formed in the first end of center rod 552. Plunger 554 includes an engagement finger which is offset from the pivot axis of anvil head assembly 512 and biased into engagement with an edge of cam latch 526. Engagement of the finger of plunger 554 with the edge of cam latch 526 presses a leading portion of the edge of cam latch 526 against an inner periphery of cutting ring 522 to urge anvil head assembly 512 to an operative or non-tilted position on center rod 552.

Anvil head assembly 512 may be tilted relative to anvil center rod assembly 514 in a pre-fired tilted position. Tilting of anvil head assembly 512 relative to anvil center rod assembly 514 causes the body portion of cam latch member 526 to engage a finger of plunger 554. As cam latch member 526 rotates with the tilting of anvil head assembly 512, plunger 554 is retracted with the bore of anvil center rod assembly 514, thereby compressing spring 556. In this manner, finger 566 of plunger 554 is distally biased against the body portion of cam latch member 526.

The cam latch member 526 is also configured to engage the retainer member 527 via a finger. Once engaged, the cam latch member 526 maintains the anvil head assembly 512 in the non-tilted position. As the retainer member 527 is deformed or broken by the cutting ring 522, the cam latch member 526 also disengages from the anvil head assembly 512, which allows the anvil head assembly 512 to tilt to the pre-fired tilted position during unclamping. For further details regarding the construction and operation of the anvil assembly, reference may be made to U.S. Pat. No. 9,554,802, filed on Nov. 13, 2013, the entire contents of which being incorporated by reference herein.

Figure 9:
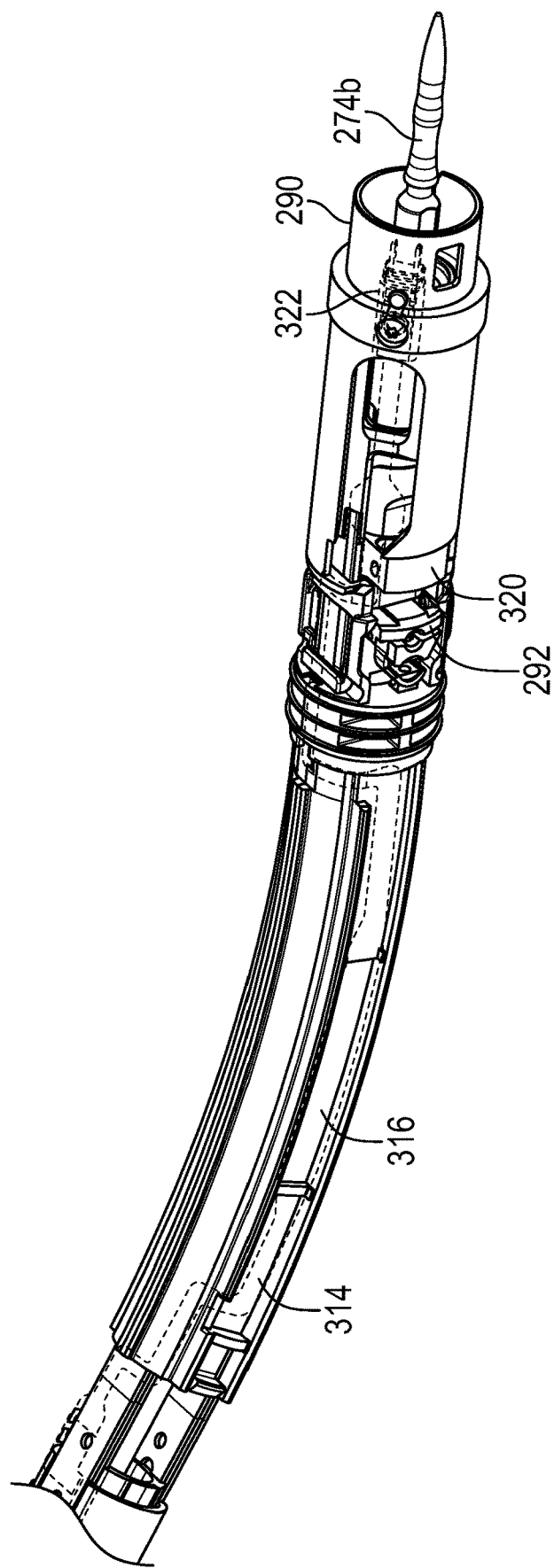
FIG. 9 is a perspective view of the adapter assembly, shown partially disassembled, with a strain gauge assembly.
Figure 10:
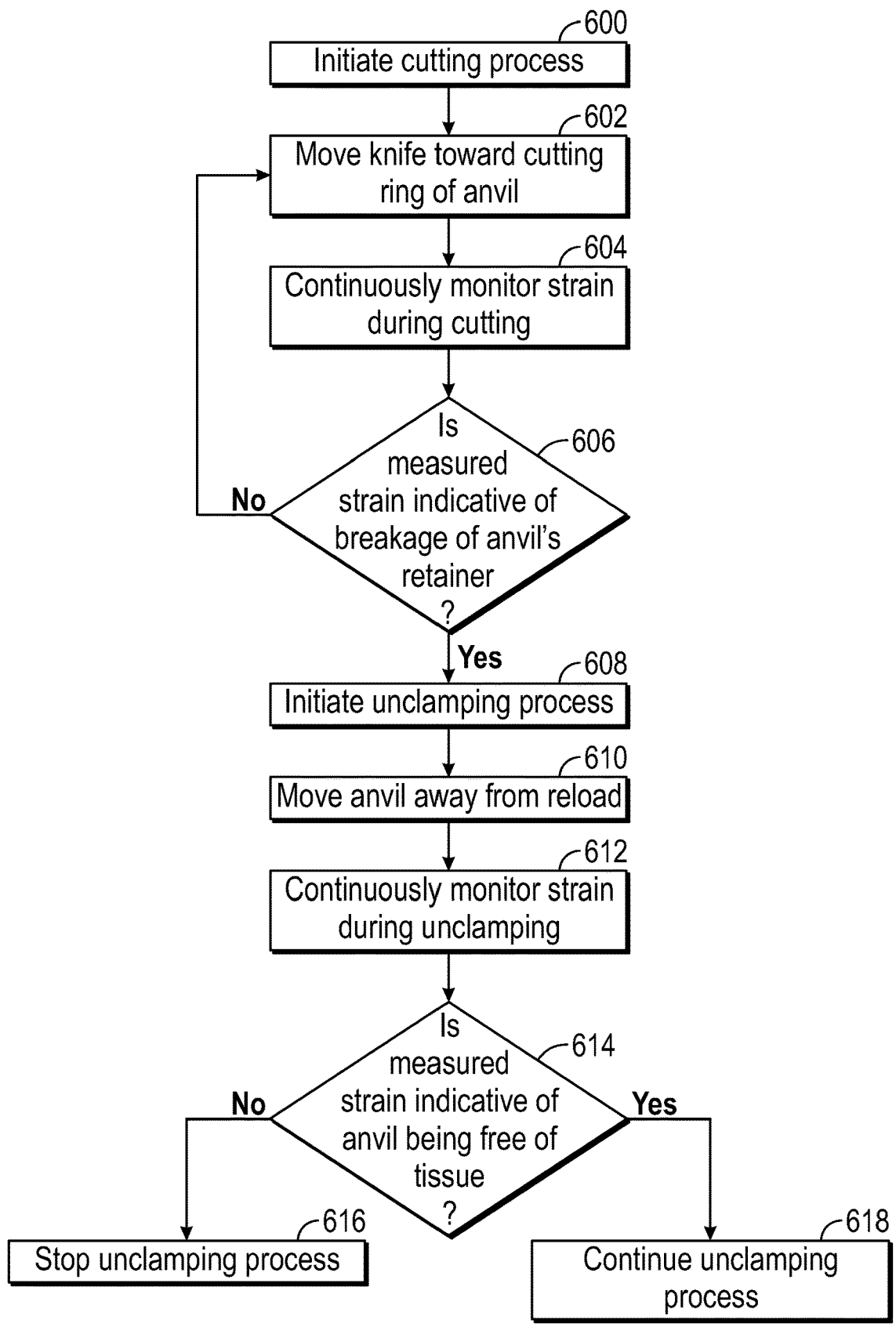
FIG. 10 is a flow chart of a method for determining anvil release during an anastomosis procedure according to an embodiment of the present disclosure.

With reference to FIG. 9, the strain gauge 408b of adapter assembly 200 is disposed within a strain gauge housing 320. The strain gauge 408b measures and monitors the retraction of trocar member 274 as well as the ejection and formation of the staples 423 from the reload 400. During the closing of end effector 300, when anvil assembly 500 contacts tissue, an obstruction, a tissue-contacting surface of the reload 400, staple ejection, or the like, a reaction force is exerted on anvil assembly 500 which is in a generally distal direction. This distally directed reaction force is communicated from anvil assembly 500 to the strain gauge 408b. The strain gauge 408b then communicates signals to main controller circuit board 142 of power handle 101 of handle assembly 100. Graphics (FIG. 8) are then displayed on the display 146 of handle assembly 100 to provide the user with real-time information related to the status of the firing of handle assembly 100.

The trocar assembly 270 is axially and rotationally fixed within outer tube 206 of adapter assembly 200. With reference to FIG. 8, adapter assembly 200 includes a support block 292 fixedly disposed within outer tube 206. The strain gauge housing 320 is disposed between the support block 292 and a connector sleeve 290. The reload 400 is removably coupled to the connector sleeve 290.

In operation, strain gauge 408b of adapter assembly 200 measures and monitors the retraction of trocar member 274, which passes through the strain gauge 408b. The strain gauge 408b of adapter assembly 200 also measures and monitors ejection of the staples 423 from the reload 400, since the first and second flexible bands 2fthir55a, 255b also pass through the strain gauge 408b. During clamping, stapling, and cutting, a reaction force is exerted on anvil assembly 500 and the reload 400, which is communicated to support block 292, which then communicates the reaction force to a strain sensor of the strain gauge 408b.

Strain sensor of strain gauge 408b may be any device configured to measure strain (a dimensionless quantity) on an object that it is adhered to (e.g., support block 292), such that, as the object deforms, a metallic foil of the strain sensor is also deformed, causing an electrical resistance thereof to change, which change in resistance is then used to calculate loads experienced by trocar assembly 270. Strain gauge 408b provides closed-loop feedback to a firing/clamping load exhibited by first, second and third force/rotation transmitting/converting assemblies.

Strain sensor of strain gauge 408b then communicates signals to main controller circuit board 142. Graphics are then displayed on display 146 of power-pack core assembly 106 of handle assembly 100 to provide the user with real-time information related to the status of the firing of handle assembly 100. Strain gauge 408b is also electrically connected to the electrical connector 312 (FIG. 3) via proximal and distal harness assemblies 314, 316.

For further details regarding the construction and operation of the circular stapler and its components, reference may be made to International Application Publication No. PCT/US2019/040440, filed on Jul. 3, 2019, the entire contents of which being incorporated by reference herein.

The reload 400 includes a storage device 402 and the circular adapter assembly 200 also includes a storage device 310 (FIG. 4). The storage devices 402 and 310 include non-volatile storage medium (e.g., EEPROM) that is configured to store any data pertaining to the reload 400 and the circular adapter assembly 200, respectively, including but not limited to, usage count, identification information, model number, serial number, staple size, stroke length, maximum actuation force, minimum actuation force, factory calibration data, and the like. In embodiments, the data may be encrypted and is only decryptable by devices (e.g., main controller 147) having appropriate keys. The data may also be used by the main controller 147 to authenticate the circular adapter assembly 200 and/or the reload 400. The storage devices 402 and 310 may be configured in read only or read/write modes, allowing the main controller 147 to read as well as write data onto the storage device 402 and 310.

Prior to operation of the powered circular stapler 10, the power handle 101 is enclosed within the shell housing 11 the adapter assembly 200 is coupled to handle assembly 100. After attachment of circular adapter assembly 200, handle assembly 100 initially verifies that circular adapter assembly 200 is coupled thereto by establishing communications with the storage device 310 of the circular adapter assembly 200 and authenticates circular adapter assembly 200. The data (e.g., usage count) stored on the storage device 310 is encrypted and is authenticated by the power handle 101 prior to determining whether the usage count stored on the storage device 310 exceeds the threshold (e.g., if the adapter assembly 200 has been previously used). Power handle 101 then performs verification checks (e.g., end of life checks, trocar member 274 missing, etc.) and calibrates circular adapter assembly 200 after the handle assembly 100 confirms that the trocar member 274 is attached.

The user commences a surgical procedure by positioning the adapter assembly 200, including the trocar member 274 and the anvil assembly 510, within the colorectal or upper gastrointestinal region. The user presses the toggle control button 30 to extend the trocar member 274 until it pierces tissue. After extension of the trocar member 274, the anvil assembly 510 that was previously positioned by surgeon is attached to the trocar member 274 and the user begins the clamping process on the tissue interposed between reload 400 and the anvil assembly 510 by pressing on the bottom portion of the toggle control button 30.

The clamping process may include controlled tissue compression until a desired threshold is reached. Once tissue is compressed, the user may initial the stapling process by pressing the toggle control button 30. In embodiments, the stapling process may be commenced automatically once tissue compression is confirmed by the main controller 147. After stapling is completed, which may be also monitored by the main controller 147, the cutting process may be initiated automatically or by pressing the toggle control button 30.

FIG. 9 shows a flow chart of a method for determining whether the anvil assembly 500 is released from the anastomosis. The method includes initiating the cutting process at step 600 by pressing the toggle control button 30 and/or automatically based on determination that the stapling process is complete by the main controller 147, e.g., based on strain, distance, and/or time measurements.

At step 602, the third motor 152c moves the outer flexible band assembly 265 of adapter assembly 200, and in turn, advances the annular knife 444 from the reload 400 until the annular knife 444 contacts the cutting ring 522. At step 604, the strain on the outer flexible band assembly 265 is measured by the strain gauge 408b. The measured strain is compared at step 606 to strain threshold and/or strain patterns indicative of the retaining member, e.g., a sudden drop in strain. If the strain measurement does not correspond to the completion of the cutting process, the method continues moving the annular knife 444. In addition, the method may also include outputting an error the display 146, e.g., if a timeout occurs and the strain does not indicate completion.

Once the cutting process is complete, at step 608 the unclamping process is initiated, by pressing the toggle control button 30 and/or automatically based on determination that the cutting process is complete by the main controller 147, e.g., based on strain, distance, and/or time measurements.

At step 610, the first motor 152a actuates the clamping transmission assembly 240 to move the anvil assembly 500 in the distal direction and away from the reload 400. At step 612, the strain on the clamping transmission assembly 240 is measured by the strain gauge 408b. The measured strain is compared at step 614 to strain threshold and/or patterns indicative of the anvil assembly 500 being attached to the tissue, e.g., strain exceeding threshold of a freely movable anvil assembly 500. If the strain measurement does not indicate that the anvil assembly 500 is free of the anastomosis, at step 616, the main controller 147 may stop the unclamping process and/or output an error the display 146. The error may be displayed if a timeout occurs, and the strain indicates that the anvil assembly 500 is adhering to anastomosis or is otherwise not movable. If the strain is indicative of the anvil assembly 500 being free and movable, then the at step 618, the unclamping process continues until it is complete. In addition to various alerts, the display 146 may also output progress bars and other indicia representative of each of the clamping, unclamping, stapling, and cutting processes.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A surgical device comprising:
   a reload assembly including a plurality of staples;
   an anvil assembly movable relative to the reload assembly, the anvil assembly including:
   a rod;
   an anvil head pivotable from a tilt position to a non-tilt position relative to the rod; and
   a retainer configured to maintain the anvil head in the non-tilt position;
   a power source;
   a motor coupled to the power source;
   a transmission assembly movable by the motor and configured to move the anvil assembly relative to the reload assembly;
   a strain sensor configured to measure strain imparted on the transmission assembly; and
   a controller configured to:
   determine the anvil assembly has tilted based on a change in measured strain in response to at least one of deformation or breakage of the retainer; and
   determine whether the anvil assembly is adhered to tissue grasped between the reload assembly and the anvil assembly based on the measured strain.

2. The surgical device according to claim 1, wherein the anvil assembly further includes a cutting ring coupled to the retainer.

3. The surgical device according to claim 2, wherein the cutting ring is configured to at least one of deform or break the retainer.

4. The surgical device according to claim 1, wherein the controller is further configured to determine whether the anvil assembly is movable during unclamping.

5. The surgical device according to claim 1, further comprising a longitudinal shaft enclosing the transmission assembly.

6. The surgical device according to claim 5, wherein the strain sensor is disposed in the longitudinal shaft and contacts the transmission assembly.

7. A surgical device comprising:
   a reload assembly including a plurality of staples;

an anvil assembly movable relative to the reload assembly, the anvil assembly including:
  a rod;
  an anvil head pivotable from a tilt position to a non-tilt position relative to the rod; and
  a retainer configured to maintain the anvil head in the non-tilt position;
a power source;
a first motor coupled to the power source;
a first transmission assembly movable by the first motor and configured to move the anvil assembly relative to the reload assembly;
a second motor coupled to the power source;
a second transmission assembly movable by the second motor and configured to move a knife assembly to cut tissue grasped between the reload assembly and the anvil assembly;
a strain sensor configured to measure strain imparted on the first transmission assembly and the second transmission assembly; and
a controller configured to:
  determine the anvil assembly has tilted based on a change in measured strain in response to of at least one of deformation or breakage of the retainer by the knife assembly; and
  determine whether the anvil assembly is adhered to the tissue based on the measured strain.

8. The surgical device according to claim 7, wherein the anvil assembly further includes a cutting ring is coupled to the retainer and to contact the knife assembly.

9. The surgical device according to claim 8, wherein the cutting ring is configured to at least one of deform or break the retainer.

10. The surgical device according to claim 7, wherein the controller is further configured to determine whether the anvil assembly is movable during unclamping.

11. The surgical device according to claim 7, further comprising a longitudinal shaft enclosing at least a portion of each of the first transmission assembly and the second transmission assembly.

12. The surgical device according to claim 11, wherein the strain sensor is disposed in the longitudinal shaft and contacts the first transmission assembly and the second transmission assembly.

13. A method for controlling a powered surgical stapler, the method comprising:
  activating a first motor to move a first transmission assembly coupled to an anvil assembly including an anvil head and a retainer securing the anvil head in a non-tilted position that is movable relative to a reload assembly having a plurality of staples;
  activating a second motor to move a second transmission assembly coupled to a knife assembly configured to cut tissue grasped between the reload assembly and the anvil assembly;
  measuring through a strain sensor, strain imparted on the first transmission assembly and the second transmission assembly;
  determining, at a controller, whether the anvil assembly has tilted based on a change in measured strain in response to of at least one of deformation or breakage of the retainer by the knife assembly; and
  determining, at the controller, whether the anvil assembly is adhered to the tissue based on the measured strain.

14. The method according to claim 13, determining, at the controller, whether the anvil assembly is movable during unclamping.

* * * * *